United States Patent
Cavacini et al.

(10) Patent No.: US 12,168,699 B2
(45) Date of Patent: Dec. 17, 2024

(54) ANTI-POLYMERIC IgA ANTIBODIES AND METHODS OF USE

(71) Applicant: University of Massachusetts, Westborough, MA (US)

(72) Inventors: Lisa Cavacini, Boston, MA (US); Mark S. J. Klempner, Boston, MA (US)

(73) Assignee: University of Massachusetts, Westborough, MA (US)

( * ) Notice: Subject to any disclaimer, the term of this patent is extended or adjusted under 35 U.S.C. 154(b) by 709 days.

(21) Appl. No.: 17/598,385

(22) PCT Filed: Mar. 27, 2020

(86) PCT No.: PCT/US2020/025131
§ 371 (c)(1),
(2) Date: Sep. 27, 2021

(87) PCT Pub. No.: WO2020/205477
PCT Pub. Date: Oct. 8, 2020

(65) Prior Publication Data
US 2022/0144970 A1    May 12, 2022

Related U.S. Application Data

(60) Provisional application No. 62/826,288, filed on Mar. 29, 2019.

(51) Int. Cl.
C07K 16/42    (2006.01)
(52) U.S. Cl.
CPC ...... *C07K 16/4241* (2013.01); *C07K 2317/24* (2013.01); *C07K 2317/33* (2013.01); *C07K 2317/565* (2013.01); *C07K 2317/567* (2013.01)

(58) Field of Classification Search
CPC ............ C07K 16/4241; C07K 16/4283; C07K 2317/24; C07K 2317/33; C07K 2317/565; C07K 2317/567
See application file for complete search history.

(56) References Cited

FOREIGN PATENT DOCUMENTS

WO    WO-2014/071455 A1    5/2014

OTHER PUBLICATIONS

De Fijter et al., "Immunoglobulin A subclass measurement in serum and saliva: sensitivity of detection of dimeric IgA2 in ELISA depends on the antibody used," J Immunol Methods. 187(2):221-32 (1995).
GenBank Accession No. ATI97782.1, "Immunoglobulin heavy chain variable region, partial [Mus musculus]," <https://www.ncbi.nlm.nih.gov/protein/1253562178>, last modified on Oct. 16, 2017, retrieved on Jun. 19, 2020 (2 pages).
GenBank Accession No. AAA97381.1, "Vk12-13 Ig variable region, partial [Mus musculus]," <https://www.ncbi.nlm.nih.gov/protein/967165>, last modified on Apr. 16, 1996, retrieved on Jun. 19, 2020 (1 page).
International Search Report and Written Opinion for International Application No. PCT/US2020/025131, mailed Jul. 9, 2020 (12 pages).
International Preliminary Report on Patentability for International Application No. PCT/US2020/025131, issued Sep. 28, 2021 (5 pages).

*Primary Examiner* — Galina M. Yakovleva
(74) *Attorney, Agent, or Firm* — Clark & Elbing LLP

(57) ABSTRACT

The invention provides anti-polymeric IgA (pIgA) antibodies and methods of using the same.

20 Claims, 5 Drawing Sheets
Specification includes a Sequence Listing.

SEQUENCE LISTING

```
<160> NUMBER OF SEQ ID NOS: 33

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Phe Thr Phe Ser Asn Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Asn Arg Gly Gly Asp Arg Ile
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic Construct

<400> SEQUENCE: 3

Arg Gly Leu Tyr Tyr Tyr Gly Ser Asp Tyr Tyr Phe Asp Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Gly Asn Ile His Asn Tyr
1               5

<210> SEQ ID NO 5
<211> LENGTH: 3
<212> TYPE: PRT
```

```
<213> ORGANISM: Artificial Sequence
<220> FEATURE:
<223> OTHER INFORMATION: Synthetic Construct

<400> SEQUENCE: 5

Asn Ala Lys
1

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

His His Tyr Tyr Ser Thr Pro Tyr Thr
1               5

<210> SEQ ID NO 7
<211> LENGTH: 25
<212> TYPE: PRT
<213> ORGANISM: Artificial Sequence
<220> FEATURE:
<223> OTHER INFORMATION: Synthetic Construct

<400> SEQUENCE: 7

Asp Val Lys Leu Val Glu Ser Gly Glu Gly Leu Val Lys Pro Gly Gly
1               5                   10                  15

Ser Leu Lys Leu Ser Cys Val Ala Ser
            20                  25

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Met Ser Trp Val Arg Gln Thr Pro Glu Lys Arg Leu Glu Trp Val Ala
1               5                   10                  15

Phe

<210> SEQ ID NO 9
<211> LENGTH: 38
<212> TYPE: PRT
<213> ORGANISM: Artificial Sequence
<220> FEATURE:
<223> OTHER INFORMATION: Synthetic Construct

<400> SEQUENCE: 9

Tyr Tyr Ala Asp Thr Val Lys Gly Arg Phe Thr Ile Ser Arg Asp Asn
1               5                   10                  15

Ala Arg Asn Thr Leu Tyr Leu Gln Met Ser Ser Leu Lys Ser Glu Asp
            20                  25                  30

Thr Ala Ile Tyr Tyr Cys
        35

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 10

Trp Gly Gln Gly Thr Thr Leu Thr Val Ser Ser
1               5                   10

<210> SEQ ID NO 11
<211> LENGTH: 26
<212> TYPE: PRT
<213> ORGANISM: Artificial Sequence
<220> FEATURE:
<223> OTHER INFORMATION: Synthetic Construct

<400> SEQUENCE: 11

Asp Ile Gln Met Thr Gln Ser Pro Ala Ser Leu Ser Thr Ser Val Gly
1               5                   10                  15

Glu Thr Val Thr Ile Thr Cys Arg Ala Ser
            20                  25

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Leu Ala Trp Ser Gln Gln Lys Gln Gly Asn Ser Pro Gln Leu Leu Val
1               5                   10                  15

Tyr

<210> SEQ ID NO 13
<211> LENGTH: 36
<212> TYPE: PRT
<213> ORGANISM: Artificial Sequence
<220> FEATURE:
<223> OTHER INFORMATION: Synthetic Construct

<400> SEQUENCE: 13

Thr Leu Ala Glu Gly Val Pro Ser Arg Phe Ser Gly Ser Gly Ser Gly
1               5                   10                  15

Thr Gln Tyr Ser Leu Lys Ile Asn Ser Leu Gln Pro Glu Asp Phe Gly
            20                  25                  30

Ser Tyr Tyr Cys
        35

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Phe Gly Ser Gly Thr Lys Leu Glu Ile Lys
1               5                   10

<210> SEQ ID NO 15
<211> LENGTH: 121
<212> TYPE: PRT
<213> ORGANISM: Artificial Sequence
<220> FEATURE:
<223> OTHER INFORMATION: Synthetic Construct

<400> SEQUENCE: 15
```

Asp Val Lys Leu Val Glu Ser Gly Glu Gly Leu Val Lys Pro Gly Gly
1               5                   10                  15

Ser Leu Lys Leu Ser Cys Val Ala Ser Gly Phe Thr Phe Ser Asn Tyr
            20                  25                  30

Gly Met Ser Trp Val Arg Gln Thr Pro Glu Lys Arg Leu Glu Trp Val
        35                  40                  45

Ala Phe Ile Asn Arg Gly Gly Asp Arg Ile Tyr Tyr Ala Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Ile Tyr Tyr Cys
                85                  90                  95

Arg Gly Leu Tyr Tyr Tyr Gly Ser Asp Tyr Tyr Phe Asp Tyr Trp Gly
            100                 105                 110

Gln Gly Thr Thr Leu Thr Val Ser Ser
        115                 120

<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

Asp Ile Gln Met Thr Gln Ser Pro Ala Ser Leu Ser Thr Ser Val Gly
1               5                   10                  15

Glu Thr Val Thr Ile Thr Cys Arg Ala Ser Gly Asn Ile His Asn Tyr
            20                  25                  30

Leu Ala Trp Ser Gln Gln Lys Gln Gly Asn Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys His His Tyr Tyr Ser Thr Pro Tyr
                85                  90                  95

Thr Phe Gly Ser Gly Thr Lys Leu Glu Ile Lys
            100                 105

<210> SEQ ID NO 17
<211> LENGTH: 24
<212> TYPE: DNA
<213> ORGANISM: Artificial Sequence
<220> FEATURE:
<223> OTHER INFORMATION: Synthetic Construct

<400> SEQUENCE: 17
ggattcactt tcagtaacta tggc                                    24

<210> SEQ ID NO 18
<211> LENGTH: 24
<212> TYPE: DNA
<213> ORGANISM: Artificial Sequence
<220> FEATURE:
<223> OTHER INFORMATION: Synthetic Construct

<400> SEQUENCE: 18
attaataggg gtggtgatcg catc                                    24

```
<210> SEQ ID NO 19
<211> LENGTH: 42
<212> TYPE: DNA
<213> ORGANISM: Artificial Sequence
<220> FEATURE:
<223> OTHER INFORMATION: Synthetic Construct

<400> SEQUENCE: 19
agagggcttt attactacgg tagtgactac tactttgact ac              42

<210> SEQ ID NO 20
<211> LENGTH: 18
<212> TYPE: DNA
<213> ORGANISM: Artificial Sequence
<220> FEATURE:
<223> OTHER INFORMATION: Synthetic Construct

<400> SEQUENCE: 20
gggaatattc acaattat                                          18

<210> SEQ ID NO 21
<211> LENGTH: 9
<212> TYPE: DNA
<213> ORGANISM: Artificial Sequence
<220> FEATURE:
<223> OTHER INFORMATION: Synthetic Construct

<400> SEQUENCE: 21 aatgcaaaa                                                     9

<210> SEQ ID NO 22
<211> LENGTH: 27
<212> TYPE: DNA
<213> ORGANISM: Artificial Sequence
<220> FEATURE:
<223> OTHER INFORMATION: Synthetic Construct

<400> SEQUENCE: 22
catcattatt atagtactcc atatacg                                27

<210> SEQ ID NO 23
<211> LENGTH: 75
<212> TYPE: DNA
<213> ORGANISM: Artificial Sequence
<220> FEATURE:
<223> OTHER INFORMATION: Synthetic Construct

<400> SEQUENCE: 23
gacgtgaagc tggtggagtc tggggaaggc ttagtgaagc tggagggtc cctgaaactc    60 tcctgtgtag cctct                                                   75

<210> SEQ ID NO 24
<211> LENGTH: 51
<212> TYPE: DNA
<213> ORGANISM: Artificial Sequence
<220> FEATURE:
<223> OTHER INFORMATION: Synthetic Construct

<400> SEQUENCE: 24
atgtcttggg ttcgccagac tccagagaag aggctggagt gggtcgcatt c           51

<210> SEQ ID NO 25
<211> LENGTH: 114
<212> TYPE: DNA
<213> ORGANISM: Artificial Sequence
```

```
<220> FEATURE:
<223> OTHER INFORMATION: Synthetic Construct

<400> SEQUENCE: 25
tactatgcag acactgtgaa gggccgattc accatctcca gagacaatgc caggaacacc      60
ctgtatttgc aaatgagcag tctgaagtct gaggacacag ccatatatta ctgt            114

<210> SEQ ID NO 26
<211> LENGTH: 33
<212> TYPE: DNA
<213> ORGANISM: Artificial Sequence
<220> FEATURE:
<223> OTHER INFORMATION: Synthetic Construct

<400> SEQUENCE: 26
tggggccaag gcaccactct cacagtctcc tca                                   33

<210> SEQ ID NO 27
<211> LENGTH: 78
<212> TYPE: DNA
<213> ORGANISM: Artificial Sequence
<220> FEATURE:
<223> OTHER INFORMATION: Synthetic Construct

<400> SEQUENCE: 27
gatatccaga tgactcagtc tccagcctcc ctgtctacat ctgtgggaga aactgtcacc      60
atcacatgtc gagcaagt                                                    78

<210> SEQ ID NO 28
<211> LENGTH: 51
<212> TYPE: DNA
<213> ORGANISM: Artificial Sequence
<220> FEATURE:
<223> OTHER INFORMATION: Synthetic Construct

<400> SEQUENCE: 28
ttagcgtggt ctcagcagaa acagggaaat tctcctcaac tcctggtcta t               51

<210> SEQ ID NO 29
<211> LENGTH: 108
<212> TYPE: DNA
<213> ORGANISM: Artificial Sequence
<220> FEATURE:
<223> OTHER INFORMATION: Synthetic Construct

<400> SEQUENCE: 29
accttagcgg aaggtgtgcc atcgaggttc agtggcagtg gatcaggaac acaatattct      60
ctcaagatca acagcctgca gcctgaggat tttgggagtt attactgt                   108

<210> SEQ ID NO 30
<211> LENGTH: 30
<212> TYPE: DNA
<213> ORGANISM: Artificial Sequence
<220> FEATURE:
<223> OTHER INFORMATION: Synthetic Construct

<400> SEQUENCE: 30
ttcggatcgg ggaccaagct ggaaataaaa                                       30

<210> SEQ ID NO 31
<211> LENGTH: 363
<212> TYPE: DNA
<213> ORGANISM: Artificial Sequence
<220> FEATURE:
```

<223> OTHER INFORMATION: Synthetic Construct

<400> SEQUENCE: 31

```
gacgtgaagc tggtggagtc tggggaaggc ttagtgaagc ctggagggtc cctgaaactc    60
tcctgtgtag cctctggatt cactttcagt aactatggca tgtcttgggt tcgccagact   120
ccagagaaga ggctggagtg ggtcgcattc attaataggg gtggtgatcg catctactat   180
gcagacactg tgaagggccg attcaccatc tccagagaca atgccaggaa caccctgtat   240
ttgcaaatga gcagtctgaa gtctgaggac acagccatat attactgtag agggctttat   300
tactacggta gtgactacta ctttgactac tggggccaag gcaccactct cacagtctcc   360
tca                                                                  363
```

<210> SEQ ID NO 32
<211> LENGTH: 321
<212> TYPE: DNA
<213> ORGANISM: Artificial Sequence
<220> FEATURE:
<223> OTHER INFORMATION: Synthetic Construct

<400> SEQUENCE: 32

```
gatatccaga tgactcagtc tccagcctcc ctgtctacat ctgtgggaga aactgtcacc    60
atcacatgtc gagcaagtgg gaatattcac aattatttag cgtggtctca gcagaaacag   120
ggaaattctc ctcaactcct ggtctataat gcaaaaacct tagcggaagg tgtgccatcg   180
aggttcagtg gcagtggatc aggaacacaa tattctctca agatcaacag cctgcagcct   240
gaggattttg ggagttatta ctgtcatcat tattatagta ctccatatac gttcggatcg   300
gggaccaagc tggaaataaa a                                              321
```

<210> SEQ ID NO 33
<211> LENGTH: 137
<212> TYPE: PRT
<213> ORGANISM: Homo sapiens

<400> SEQUENCE: 33

```
Gln Glu Asp Glu Arg Ile Val Leu Val Asp Asn Lys Cys Lys Cys Ala
1               5                   10                  15
Arg Ile Thr Ser Arg Ile Ile Arg Ser Ser Glu Asp Pro Asn Glu Asp
            20                  25                  30
Ile Val Glu Arg Asn Ile Arg Ile Ile Val Pro Leu Asn Asn Arg Glu
        35                  40                  45
Asn Ile Ser Asp Pro Thr Ser Pro Leu Arg Thr Arg Phe Val Tyr His
    50                  55                  60
Leu Ser Asp Leu Cys Lys Lys Cys Asp Pro Thr Glu Val Glu Leu Asp
65                  70                  75                  80
Asn Gln Ile Val Thr Ala Thr Gln Ser Asn Ile Cys Asp Glu Asp Ser
                85                  90                  95
Ala Thr Glu Thr Cys Tyr Thr Tyr Asp Arg Asn Lys Cys Tyr Thr Ala
            100                 105                 110
Val Val Pro Leu Val Tyr Gly Gly Glu Thr Lys Met Val Glu Thr Ala
        115                 120                 125
Leu Thr Pro Asp Ala Cys Tyr Pro Asp
    130                 135
```

ANTI-POLYMERIC IgA ANTIBODIES AND METHODS OF USE

CROSS-REFERENCE TO RELATED APPLICATION(S)

This application relates to and claims priority from U.S. Patent Application No. 62/826,288 filed on Mar. 29, 2019, the entire disclosure of which is incorporated herein by reference.

STATEMENT AS TO FEDERALLY FUNDED RESEARCH

This invention was made with government support under Grant No. W911 NF-13-1-0346 awarded by the Defense Advanced Research Projects Agency. The government has certain rights in the invention.

SEQUENCE LISTING

The instant application contains a Sequence Listing which has been submitted electronically in ASCII format and is hereby incorporated by reference in its entirety. Said ASCII copy, created on Mar. 13, 2020, is named 50811-006WO2_Sequence_Listing_03.13.20_ST25 and is 11,488 bytes in size.

BACKGROUND OF THE INVENTION

The IgA isotype of immunoglobulins is a critical component of mucosal immunity and immune responses. IgA can assemble as a monomeric or polymeric molecule, with IgA dimers or tetramers formed by a polypeptide called the J chain (15-16 kDa). The J chain associates with IgA within the antibody-producing cell shortly before or at the time of secretion. Secretory IgA (sIgA) is dimeric IgA (dIgA) associated with a cleaved portion of the polymeric immunoglobulin receptor (pIgR), which is called the secretory component (SC) (70-80 kDa). dIgA binds to the pIgR on the basolateral surface of epithelial cells and is transported through the cell and released on the apical (mucosal) side cell with the cleaved extracellular domain of pIgR, the secretory component. Although the secretory component is not physically associated with the J chain of the polymeric IgA (pIgA), the J chain is required for the secretory component to associate with pIgA. sIgA participates in both the adaptive (antigen binding) and innate (adhesion due to glycans) arms of the immune system.

Despite it being established that IgA antibodies (e.g., dIgA and sIgA), are critical to mucosal protection, there are no monoclonal antibodies specific to dIgA that can be used without denaturing the molecule. Polyclonal and monoclonal antibodies to the J chain exist; however, they fail to react with intact dIgA or sIgA. Thus, there exists a need for antibodies that specifically bind to intact pIgA, namely intact dIgA and sIgA.

SUMMARY OF THE INVENTION

In one aspect, the disclosure features an isolated antibody that specifically binds polymeric immunoglobulin A (pIgA), wherein the antibody comprises the following complementarity determining regions (CDRs): (a) a CDR-H1 comprising the amino acid sequence of GFTFSNYG (SEQ ID NO: 1); (b) a CDR-H2 comprising the amino acid sequence of INRGGDRI (SEQ ID NO: 2); (c) a CDR-H3 comprising the amino acid sequence of RGLYYYGSDYYFDY (SEQ ID NO: 3); (d) a CDR-L1 comprising the amino acid sequence of GNIHNY (SEQ ID NO: 4); (e) a CDR-L2 comprising the amino acid sequence of NAK (SEQ ID NO: 5); and (f) a CDR-L3 comprising the amino acid sequence of HHYYSTPYT (SEQ ID NO: 6). In some aspects, the antibody further comprises the following heavy chain framework regions (FRs): (a) an FR-H1 comprising the amino acid sequence of DVKLVESGEGLVKPGGSLKLSCVAS (SEQ ID NO: 7); (b) an FR-H2 comprising the amino acid sequence of MSWVRQTPEKRLEWVAF (SEQ ID NO: 8); (c) an FR-H3 comprising the amino acid sequence of YYADTVKGRFTISRDNARNTLYLQMSSLKSED-TAIYYC (SEQ ID NO: 9); and (d) an FR-H4 comprising the amino acid sequence of WGQGTTLTVSS (SEQ ID NO: 10). In some aspects, the antibody further comprises the following light chain FRs: (a) an FR-L1 comprising the amino acid sequence of DIQMTQSPASLSTSVGETVTIT-CRAS (SEQ ID NO: 11); (b) an FR-L2 comprising the amino acid sequence of LAWSQQKQGNSPQLLVY (SEQ ID NO: 12); (c) an FR-L3 comprising the amino acid sequence of TLAEGVPSRFSGSGSGTQYSLKIN-SLQPEDFGSYYC (SEQ ID NO: 13); and (d) an FR-L4 comprising the amino acid sequence of FGSGTKLEIK (SEQ ID NO: 14). In some aspects, the antibody comprises a heavy chain variable (VH) domain comprising an amino acid sequence having at least 95% sequence identity to the amino acid sequence of SEQ ID NO: 15 and a light chain variable (VL) domain comprising an amino acid sequence having at least 95% sequence identity to the amino acid sequence of SEQ ID NO: 16. In some aspects, the antibody comprises a VH domain comprising an amino acid sequence having at least 96% sequence identity to the amino acid sequence of SEQ ID NO: 15 and a VL domain comprising an amino acid sequence having at least 96% sequence identity to the amino acid sequence of SEQ ID NO: 16. In some aspects, the antibody comprises a VH domain comprising an amino acid sequence having at least 96% sequence identity to the amino acid sequence of SEQ ID NO: 15 and a VL domain comprising an amino acid sequence having at least 96% sequence identity to the amino acid sequence of SEQ ID NO: 16. In some aspects, the antibody comprises a VH domain comprising an amino acid sequence having at least 98% sequence identity to the amino acid sequence of SEQ ID NO: 15 and a VL domain comprising an amino acid sequence having at least 98% sequence identity to the amino acid sequence of SEQ ID NO: 16. In some aspects, the antibody comprises a VH domain comprising an amino acid sequence having at least 99% sequence identity to the amino acid sequence of SEQ ID NO: 15 and a VL domain comprising an amino acid sequence having at least 99% sequence identity to the amino acid sequence of SEQ ID NO: 16.

In another aspect, the disclosure features an isolated antibody that specifically binds pIgA, wherein the antibody comprises a VH domain comprising the amino acid sequence of SEQ ID NO: 15 and a VL domain comprising the amino acid sequence of SEQ ID NO: 16.

In some aspects, the pIgA is a dimeric IgA (dIgA). In some aspects, the dIgA is dIgA1 or dIgA2.

In some aspects, the pIgA is a secretory IgA (sIgA). In some aspects, the sIgA is sIgA1 or sIgA2.

In some aspects, the antibody specifically binds to a J chain polypeptide of pIgA. In some aspects, the antibody binds to intact pIgA. In some aspects, the pIgA is a human or a rhesus pIgA.

In some aspects, the antibody is a monoclonal, human, humanized, or chimeric antibody. In some aspects, the antibody is a monoclonal antibody.

In some aspects, the antibody is a full-length antibody. In other aspects, the antibody is an antibody fragment that specifically binds pIgA. In some aspects, the antibody fragment is selected from the group consisting of Fab, Fab', Fab'-SH, Fv, single chain variable fragment (scFv), and (Fab')$_2$ fragments.

In some aspects, the antibody is cross-reactive with human pIgA and rhesus pIgA.

In some aspects, the antibody does not bind monomeric IgA (mIgA).

In some aspects, the antibody is an IgG antibody. In some aspects, the antibody is an IgG1 antibody.

In another aspect, the disclosure features a composition comprising an antibody of any one of the aspects herein.

In another aspect, the disclosure features an isolated nucleic acid encoding an antibody of any one of the aspects herein.

In another aspect, the disclosure features a vector comprising a nucleic acid of the above aspect.

In another aspect, the disclosure features a host cell comprising a vector of the above aspect. In some aspects, the host cell is a mammalian cell. In some aspects, the mammalian cell is a Chinese hamster ovary (CHO) cell. In other aspects, the host cell is a prokaryotic cell. In some aspects, the prokaryotic cell is an *E. coli* cell.

In another aspect, the disclosure features a method of producing an antibody that specifically binds pIgA, the method comprising culturing a host cell of any one of the aspects herein in a culture medium. In some aspects, the method further comprises recovering the antibody from the host cell or the culture medium.

In another aspect, the disclosure features a method of purifying pIgA from a sample, the method comprising contacting the sample with an antibody of any one of the aspects herein. In another aspect, the disclosure features a method of quantitating pIgA in a sample, the method comprising contacting the sample with an antibody of any one of the aspects herein. In some aspects, the sample is an antibody preparation, a plasma sample, or a mucosal secretion sample. In some aspects, the sample is isolated from a human. In some aspects, the pIgA is dIgA. In some aspects, the dIgA is dIgA1 or dIgA2. In other aspects, the pIgA is sIgA. In some aspects, the sIgA is sIgA1 or sIgA2.

In another aspect, the disclosure features a kit comprising an antibody of any one of the aspects herein and a package insert comprising instructions for using the antibody for purifying pIgA from a sample. In another aspect, the disclosure features a kit comprising an antibody of any one of the aspects herein and a package insert comprising instructions for using the antibody for quantitating pIgA from a sample. In some aspects, the sample is an antibody preparation, a plasma sample, or a mucosal secretion sample. In some aspects, the sample is isolated from a human. In some aspects, the pIgA is dIgA. In some aspects, the dIgA is dIgA1 or dIgA2. In other aspects, the pIgA is sIgA. In some aspects, the sIgA is sIgA1 or sIgA2.

DETAILED DESCRIPTION OF THE INVENTION

I. Definitions

Figure 1:
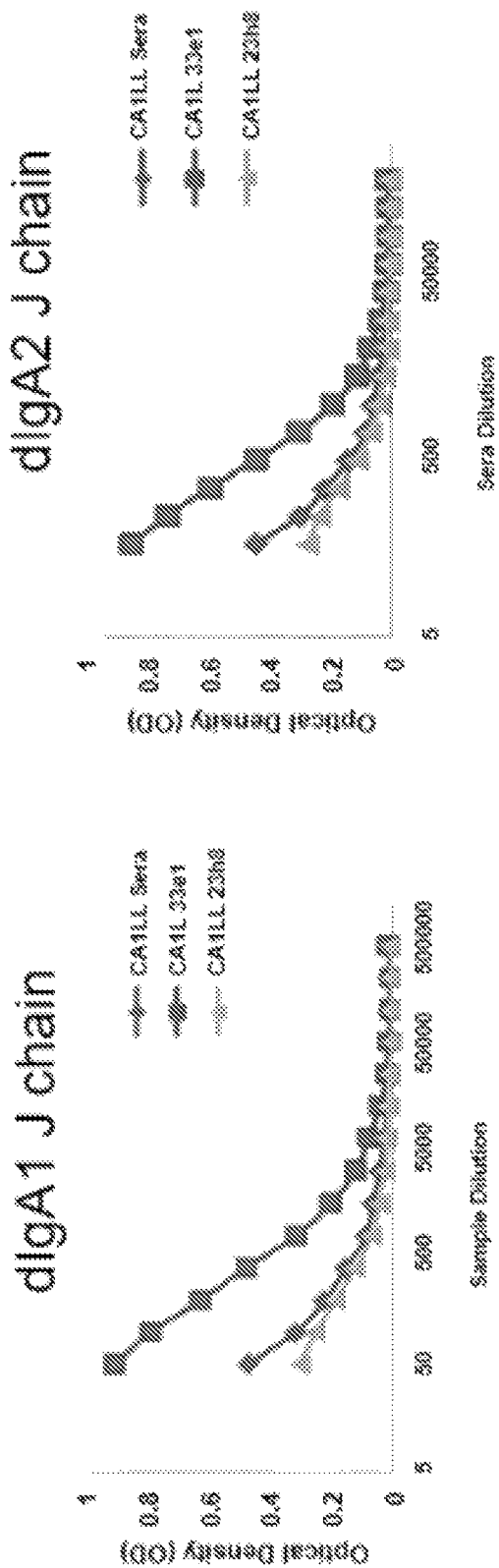
FIG. 1 is a series of graphs showing the reactivity of the anti-human J chain antibodies CA1L 33e1 and CA1LL 23h8 with dimeric IgA1 (dIgA1) and dimeric IgA2 (dIgA2).

The terms "anti-polymeric IgA antibody," "an antibody that binds to polymeric IgA," and "an antibody that specifically binds to pIgA" refer to an antibody that is capable of binding a pIgA antibody, e.g., a dimeric IgA (dIgA) or secretory IgA (sIgA), with sufficient affinity such that the antibody is useful as an analytical (e.g., quantitative), preventative, diagnostic, and/or therapeutic agent in targeting pIgA. In one embodiment, the extent of binding of an anti-pIgA antibody to an unrelated, non-pIgA protein (e.g., monomeric IgA (mIgA)) is less than about 10% of the binding of the antibody to IgA as measured, e.g., by a radioimmunoassay (RIA). In certain embodiments, an antibody that binds to IgA has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

The term "polymeric immunoglobulin A" or "polymeric IgA (pIgA)" refers to an IgA antibody including at least two IgA molecules (e.g., two, three, or four or more IgA molecules) linked by a joining (J) chain. pIgA includes dIgA and sIgA. dIgA is a dimer of two IgA molecules linked by a J chain, without a secretory component (SC) polypeptide. sIgA is a pIgA (e.g., dIgA) associated with an SC polypeptide.

The term "antibody" as used herein in the broadest sense encompasses various antibody structures, including but not limited to monoclonal antibodies, polyclonal antibodies, multispecific antibodies (e.g., bispecific antibodies), and antibody fragments so long as they exhibit the desired antigen-binding activity. An "antibody" can refer, for example, to a glycoprotein comprising at least two heavy chains (HCs) and two light chains (LCs) inter-connected by disulfide bonds, or an antigen binding portion thereof. Each heavy chain is comprised of a heavy chain variable region (VH) and a heavy chain constant region (CH). The heavy chain constant region may be comprised of three domains, CH1, CH2, and/or CH3. Each light chain is comprised of a light chain variable region (VL) and a light chain constant region (CL). The VH and VL regions can be further subdivided into regions of hypervariability, termed "complementarity determining regions" (CDRs), interspersed with regions that are more conserved, termed "framework regions" (FRs). Each VH and VL may be composed, for example, of three CDRs and four FRs, arranged from amino-terminus to carboxyl-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The terms "full-length antibody" and "whole antibody" are used herein interchangeably to refer to an antibody having a structure substantially similar to a native antibody structure or having heavy chains that contain an Fc region as defined herein. The term "intact antibody" is used to refer to an antibody that is a full-length antibody or comprises a substantial portion of a full-length antibody, such that the antibody maintains a structure substantially similar to a native antibody structure.

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) Nature 368(6474): 856-859); Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). However, the term "human antibody" does not include antibodies in which CDR sequences derived from the germline of another mammalian species, such as a mouse, have been grafted onto human framework sequences (i.e., humanized antibodies).

The term "monoclonal antibody," as used herein, refers to an antibody which displays a single binding specificity and affinity for a particular epitope. Accordingly, the term "human monoclonal antibody," or "HuMab," refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

An "antibody fragment" refers to a molecule other than a full-length antibody that comprises a portion of a full-length antibody that specifically binds to the antigen (e.g., pIgA) to which the full-length antibody binds. Examples of antibody fragments include, but are not limited to, Fv, Fab, Fab', Fab'-SH, F(ab')$_2$; diabodies; linear antibodies; single-chain antibody molecules (e.g., scFv); and multispecific antibodies formed from antibody fragments. These antibody fragments are obtained using conventional techniques, and the fragments are screened for utility in the same manner as are full-length antibodies. Antibody fragments can be produced by recombinant DNA techniques, or by enzymatic or chemical cleavage of full-length immunoglobulins.

The term "about" as used herein refers to the usual error range for the respective value readily known to the skilled person in this technical field. Reference to "about" a value or parameter herein includes (and describes) embodiments that are directed to that value or parameter per se.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described below.

The term "$K_D$," as used herein, is intended to refer to the dissociation equilibrium constant of a particular antibody-antigen interaction. Typically, the antibodies of the invention bind to pIgA with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower when determined by surface plasmon resonance (SPR) technology in a BIACORE® 3000 instrument using recombinant pIgA as the analyte and the antibody as the ligand.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14, or 15 amino acids in a unique spatial conformation. Methods of determining spatial conformation of epitopes include techniques in the art and those described herein, for example, X-ray crystallography and 2-dimensional nuclear magnetic resonance. See, for example, Epitope Mapping Protocols in Methods in Molecular Biology, Vol. 66, G. E. Morris, Ed. (1996). Epitopes can also be defined by point mutations in the target protein (e.g., pIgA), which affect the binding of the antibody (e.g., monoclonal antibody).

The term "host cell," as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "isolated antibody" is one which has been identified and separated and/or recovered from a component of its natural environment and/or is substantially free of other antibodies having different antigenic specificities (e.g., an isolated antibody that specifically binds to pIgA is substantially free of antibodies that specifically bind antigens other than pIgA). Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using COOMASSIE® Blue or, preferably, silver stain. Isolated antibody includes the antibody in situ within recombinant cells since at least one component of the antibody's natural environment will not be present. Similarly, isolated antibody includes the antibody in medium around recombinant cells. Ordinarily, however, isolated antibody will be prepared by at least one purification step.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid," as used herein in reference to nucleic acids molecules encoding antibodies or antibody portions (e.g., VH, VL, CDRs) that bind to pIgA, is intended to refer to a nucleic acid molecule in which the nucleotide sequences encoding the antibody or antibody portion are free of other nucleotide sequences encoding antibodies that bind antigens other than pIgA, which other sequences may naturally flank the nucleic acid in human genomic DNA.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument, which can be performed, for example, using recombinant pIgA as the analyte and the antibody as the ligand. In some embodiments, binding by the antibody to the predetermined antigen is with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, the term "vector" is meant to include, but is not limited to, a nucleic acid molecule (e.g., a nucleic acid molecule that is capable of transporting another nucleic acid to which it has been linked), a virus (e.g., a lentivirus or an adenovirus, e.g., a recombinant adeno-associated virus (rAAV)), cationic lipid (e.g., liposome), cationic polymer (e.g., polysome), virosome, nanoparticle, or dentrimer. Accordingly, one type of vector is a viral vector, wherein additional DNA segments (e.g., transgenes, e.g., transgenes encoding the heavy and/or light chain genes of an anti-pIgA antibody of the invention) may be ligated into the viral genome, and the viral vector may then be administered (e.g., by electroporation, e.g., electroporation into muscle tissue) to the subject in order to allow for transgene expression in a manner analogous to gene therapy. Another type of vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids.

II. Compositions and Methods

In one aspect, the invention is based, in part, on anti-polymeric immunoglobulin A (pIgA) antibodies. Antibodies of the invention are useful, for example, for selecting or quantitating the amount of a pIgA, such as dimeric IgA (dIgA) or secretory IgA (sIgA), in a sample.

A. Anti-pIgA Antibodies

The invention provides isolated antibodies that bind to pIgA antibodies.

In one aspect, the invention provides isolated antibodies that specifically bind to pIgA. In some instances, the antibody may include the following complementarity determining regions (CDRs): (a) a CDR-H1 comprising the amino acid sequence of GFTFSNYG (SEQ ID NO: 1) or the amino acid sequence encoded by the nucleic acid sequence of SEQ ID NO: 17; (b) a CDR-H2 comprising the amino acid sequence of INRGGDRI (SEQ ID NO: 2) or the amino acid sequence encoded by the nucleic acid sequence of SEQ ID NO: 18; (c) a CDR-H3 comprising the amino acid sequence of RGLYYYGSDYYFDY (SEQ ID NO: 3) or the amino acid sequence encoded by the nucleic acid sequence of SEQ ID NO: 19, or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-3 and/or to the amino acid sequence encoded by any one of SEQ ID NOs: 17-19, and/or (ii) one, two, or three amino acid substitutions relative to the amino acid sequence of any one of SEQ ID NOs: 1-3 or the amino acid sequence encoded by any one of SEQ ID NOs: 17-19. In some instances, the antibody includes the following CDRs: (a) a CDR-L1 comprising the amino acid sequence of GNIHNY (SEQ ID NO: 4) or the amino acid sequence encoded by the nucleic acid sequence of SEQ ID NO: 20; (b) a CDR-L2 comprising the amino acid sequence of NAK (SEQ ID NO: 5) or the amino acid sequence encoded by the nucleic acid sequence of SEQ ID NO: 21; and (c) a CDR-L3 comprising the amino acid sequence of HHYYSTPYT (SEQ ID NO: 6) or the amino acid sequence encoded by the nucleic acid sequence of SEQ ID NO: 22, or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 4-6 or the amino acid sequence encoded by the nucleic acid sequence of any one of SEQ ID NOs: 20-22, and/or (ii) one, two, or three amino acid substitutions relative to the amino acid sequence of any one of SEQ ID NOs: 4-6 or the amino acid sequence encoded by the nucleic acid sequence of any one of SEQ ID NOs: 20-22.

In some instances, the anti-pIgA antibodies may include the following heavy chain framework regions (FRs): (a) an FR-H1 comprising the amino acid sequence of DVKLVES-GEGLVKPGGSLKLSCVAS (SEQ ID NO: 7) or the amino acid sequence encoded by the nucleic acid sequence of SEQ ID NO: 23; (b) an FR-H2 comprising the amino acid sequence of MSWVRQTPEKRLEWVAF (SEQ ID NO: 8) or the amino acid sequence encoded by the nucleic acid sequence of SEQ ID NO: 24; (c) an FR-H3 comprising the amino acid sequence of YYADTVKGRFTISRDNARN-TLYLQMSSLKSEDTAIYYC (SEQ ID NO: 9) or the amino acid sequence encoded by the nucleic acid sequence of SEQ ID NO: 25; and (d) an FR-H4 comprising the amino acid sequence of WGQGTTLTVSS (SEQ ID NO: 10) or the amino acid sequence encoded by the nucleic acid sequence of SEQ ID NO: 26, or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 7-10 or the amino acid sequence encoded by the nucleic acid sequence of any one of SEQ ID NOs: 23-26.

In some instances, the anti-pIgA antibodies may include the following light chain FRs: (a) an FR-L1 comprising the amino acid sequence of DIQMTQSPASLSTSVGETVTIT-CRAS (SEQ ID NO: 11) or the amino acid sequence encoded by the nucleic acid sequence of SEQ ID NO: 27; (b) an FR-L2 comprising the amino acid sequence of LAWSQQKQGNSPQLLVY (SEQ ID NO: 12) or the amino acid sequence encoded by the nucleic acid sequence of SEQ ID NO: 28; (c) an FR-L3 comprising the amino acid sequence of TLAEGVPSRFSGSGSGTQYSLKIN-SLQPEDFGSYYC (SEQ ID NO: 13) or the amino acid sequence encoded by the nucleic acid sequence of SEQ ID NO: 29; and (d) an FR-L4 comprising the amino acid sequence of FGSGTKLEIK (SEQ ID NO: 14) or the amino acid sequence encoded by the nucleic acid sequence of SEQ ID NO: 30, or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 11-14 or the amino acid sequence encoded by the nucleic acid sequence of any one of SEQ ID NOs: 27-30.

For example, the antibody may include the following six CDRs: (a) a CDR-H1 comprising the amino acid sequence of GFTFSNYG (SEQ ID NO: 1); (b) a CDR-H2 comprising the amino acid sequence of INRGGDRI (SEQ ID NO: 2); (c) a CDR-H3 comprising the amino acid sequence of RGLYYYGSDYYFDY (SEQ ID NO: 3); (d) a CDR-L1 comprising the amino acid sequence of GNIHNY (SEQ ID NO: 4); (e) a CDR-L2 comprising the amino acid sequence of NAK (SEQ ID NO: 5); and (f) a CDR-L3 comprising the amino acid sequence of HHYYSTPYT (SEQ ID NO: 6), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6, and/or (ii) one, two, or three amino acid substitutions relative to the amino acid sequence of any one of SEQ ID NOs: 1-6. In some instances, the antibody includes the following four heavy chain FRs: (a) an FR-H1 comprising the amino acid sequence of DVKLVES-GEGLVKPGGSLKLSCVAS (SEQ ID NO: 7); (b) an FR-H2 comprising the amino acid sequence of MSWVRQT-PEKRLEWVAF (SEQ ID NO: 8); (c) an FR-H3 comprising the amino acid sequence of YYADTVKGRFTISRDNARN-TLYLQMSSLKSEDTAIYYC (SEQ ID NO: 9); and (d) an FR-H4 comprising the amino acid sequence of WGQGT-TLTVSS (SEQ ID NO: 10), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 7-10. In some instances, the antibody includes the following four light chain FRs: (a) an FR-L1 comprising the amino acid sequence of DIQMTQSPASLSTSVGETVTITCRAS (SEQ ID NO: 11); (b) an FR-L2 comprising the amino acid sequence of LAWSQQKQGNSPQLLVY (SEQ ID NO: 12); (c) an FR-L3 comprising the amino acid sequence of TLAE-GVPSRFSGSGSGTQYSLKINSLQPEDFGSYYC (SEQ ID NO: 13); and (d) an FR-L4 comprising the amino acid sequence of FGSGTKLEIK (SEQ ID NO: 14), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 11-14. In some instances, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 15; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH sequence as in (a) and a VL sequence as in (b).

In a further example, the antibody includes the following six CDRs: (a) a CDR-H1 comprising the amino acid sequence encoded by the nucleic acid sequence of SEQ ID NO: 17; (b) a CDR-H2 comprising the amino acid sequence encoded by the nucleic acid sequence of SEQ ID NO: 18; (c) a CDR-H3 comprising the amino acid sequence encoded by the nucleic acid sequence of SEQ ID NO: 19; (d) a CDR-L1 comprising the amino acid sequence encoded by the nucleic acid sequence of SEQ ID NO: 20; (e) a CDR-L2 comprising the amino acid sequence encoded by the nucleic acid sequence of SEQ ID NO: 21; and (f) a CDR-L3 comprising the amino acid sequence encoded by the nucleic acid sequence of SEQ ID NO: 22, or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to the amino acid sequence encoded by the nucleic acid sequence of any one of SEQ ID NOs: 17-22, and/or (ii) one, two, or three amino acid substitutions relative to the amino acid sequence encoded by the nucleic acid sequence of any one of SEQ ID NOs: 17-22. In some instances, the antibody includes the following four heavy chain FRs: (a) an FR-H1 comprising the amino acid sequence encoded by the nucleic acid sequence of SEQ ID NO: 23; (b) an FR-H2 comprising the amino acid sequence encoded by the nucleic acid sequence of SEQ ID NO: 24; (c) an FR-H3 comprising the amino acid sequence encoded by the nucleic acid sequence of SEQ ID NO: 25; and (d) an FR-H4 comprising the amino acid sequence encoded by the nucleic acid sequence of SEQ ID NO: 26, or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to the amino acid sequence encoded by the nucleic acid sequence of any one of SEQ ID NOs: 23-26. In some instances, the antibody includes the following four light chain FRs: (a) an FR-L1 comprising the amino acid sequence encoded by the nucleic acid sequence of SEQ ID NO: 27; (b) an FR-L2 comprising the amino acid sequence encoded by the nucleic acid sequence of SEQ ID NO: 28; (c) an FR-L3 comprising the amino acid sequence encoded by the nucleic acid sequence of SEQ ID NO: 29; and (d) an FR-L4 comprising the amino acid sequence encoded by the nucleic acid sequence of SEQ ID NO: 30, or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to the amino acid sequence encoded by the nucleic acid sequence of any one of SEQ ID NOs: 27-30. In some instances, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, the amino acid sequence encoded by the nucleic acid sequence of SEQ ID NO: 31; (b) a light chain variable domain (VL) sequence having at least 90% sequence identity (e.g., at least 91%, 92%, 93%, 94%, 95%, 96%, 97%, 98%, or 99% sequence identity) to, or the sequence of, the amino acid sequence encoded by the nucleic acid sequence of SEQ ID NO: 32; or (c) a VH sequence as in (a) and a VL sequence as in (b).

In particular instances, the antibody is the anti-pIgA antibody CA1L 33e1.

Antibodies of the invention may, for example, be monoclonal, human, humanized, or chimeric. The antibodies can be full-length antibodies or antibody fragments thereof (e.g., an antibody fragment that specifically binds pIgA). The antibody fragment may be selected from the group consisting of Fab, Fab'-SH, Fv, scFv, and (Fab')$_2$ fragments. In some instances, the antibody is an IgG antibody (e.g., an IgG1 antibody). An antibody of the invention may have a half-life of 3 days (e.g., 1 week, e.g., 2 weeks, e.g., 1 month, e.g., 2 months, e.g., 3 months, e.g., 4 months, e.g., 5 months, e.g., 6 months).

In some embodiments, the anti-pIgA antibodies of any of the aspects described herein are capable of specifically binding to the pIgA subtypes pIgA1 and pIgA2 (e.g., dIgA1, dIgA2, sIgA1, and sIgA2). In some embodiments, the anti-pIgA antibodies described herein do not bind to mIgA. Additionally, the anti-pIgA antibodies described herein may cross-react with human pIgA and rhesus pIgA.

In a further aspect, an anti-pIgA antibody according to any of the above embodiments may incorporate any of the features, singly or in combination, as described in Sections 1-7 below.

1. Antibody Affinity

In certain embodiments, an antibody provided herein may have a dissociation constant ($K_D$) of ≤10 μM, ≤1 μM, ≤100 nM, ≤10 nM, ≤1 nM, ≤0.1 nM, or ≤0.01 nM.

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN® 20) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-3000 (Biacore, Inc., Piscataway, N.J.) is performed at 25° C. with immobilized antigen CM5 chips at ~10 response units (RU). In one embodiment, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN® 20) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{on}/k_{off}$. See, for example, Chen et al., *J. Mol. Biol.* 293:865-881 (1999). If the on-rate exceeds $10^6$ M$^{-1}$s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment that specifically binds pIgA. In some embodiments, the antibody fragment specifically binds the pIgA1 and pIgA2 subtypes (e.g., dIgA1, dIgA2, sIgA1, and sIgA2). In further embodiments, the anti-pIgA antibody fragment does not bind to mIgA. The anti-pIgA antibody fragment may cross-react with human pIgA and rhesus pIgA. Antibody fragments include, but are not limited to, Fab, Fab', Fab'-SH, F(ab')$_2$, Fv, and scFv fragments, which are known in the art. Also included are diabodies, which have two antigen-binding sites that may be bivalent or bispecific, as is known in the art. Triabodies and tetrabodies are also known. Single-domain antibodies are also antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells (e.g., *E. coli* or phage), as described herein.

3. Monoclonal Antibodies

Monoclonal antibodies can be produced in a manner not possible with polyclonal antibodies. Polyclonal antisera vary from animal to animal, whereas monoclonal preparations exhibit a uniform antigenic specificity. Murine animal systems are useful to generate monoclonal antibodies, and immunization protocols, techniques for isolating and fusing splenocytes, and methods and reagents for producing hybridomas are well known. Monoclonal antibodies can be produced by a variety of techniques, including conventional monoclonal antibody methodology, e.g., standard somatic cell hybridization techniques.

One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597WO92/18619; WO 91/17271; WO 92/20791; WO 92/15679; WO 93/01288; WO 92/01047; WO 92/09690; and WO 90/02809, each of which is incorporated herein by reference in its entirety.

In addition to the use of display libraries, the specified antigen can be used to immunize a non-human animal, e.g., a rodent, e.g., a mouse, a hamster, or a rat. For example, an animal is immunized with all or a portion of a J chain of pIgA (e.g., dIgA or sIgA). The J chain of pIgA can be a human J chain, and can be modified into a maltose binding protein (MBP) fusion protein according to standard techniques. Immune spleen cells of the animal then are identified, isolated and fused with lymphoma or myeloma cells by being contacted with a fusing agent such as polyethylene glycol such as by the procedure of Kohler & Milsrein, Nature 256: 459, 1975. The fused cells then are incubated in a selective medium, such as HAT medium, which precludes the growth of unfused malignant cells. The hybridoma cells are cloned by limiting dilution and supernatants are assayed for secreted monoclonal antibody of desired specificity.

Monoclonal antibodies can also be made by harvesting antibody producing cells, e.g., splenocytes, from transgenic mice expressing human immunogloulin genes and which have been immunized with all or a portion of the J chain of pIgA. The splenocytes can be immortalized through fusion with human myelomas or through transformation with Epstein-Barr virus (EBV). These hybridomas can be made using human B cell or EBV hybridoma techniques described in the art (see, e.g., Boyle et al., European Patent Publication No. 0 614 984, incorporated herein by reference in its entirety).

A monoclonal antibody can be obtained from a non-human animal, and then modified, e.g., humanized, deimmunized, chimeric, using recombinant DNA techniques described herein and known in the art.

4. Chimeric and Humanized Antibodies

In certain embodiments, an antibody provided herein is a chimeric antibody. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

5. Human Antibodies

In certain embodiments, an antibody provided herein is a human antibody (e.g., a human monoclonal antibody (HuMab), e.g., an anti-pIgA HuMab). Human antibodies can be produced using various techniques known in the art.

In some instances, human antibodies are obtained by cloning the heavy and light chain genes directly from human B cells obtained from a human subject. The B cells are separated from peripheral blood (e.g., by flow cytometry, e.g., FACS), stained for B cell marker(s), and assessed for antigen binding. The RNA encoding the heavy and light chain variable regions (or the entire heavy and light chains) is extracted and reverse transcribed into DNA, from which the antibody genes are amplified (e.g., by PCR) and sequenced. The known antibody sequences can then be used to express recombinant human antibodies against a known target antigen (e.g., pIgA).

In some instances, human antibodies may be prepared by administering an immunogen (e.g., all or a portion of the J chain of pIgA) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. Human variable regions from intact antibodies generated by such animals may be further modified, for example, by combining with a different human constant region.

In some instances, human antibodies can also be made by hybridoma-based methods, as described in further detail below. Human myeloma and mouse-human heteromyeloma cell lines for the production of human monoclonal antibodies have been described.

One useful type of animal in which to generate human monoclonal antibodies is a transgenic mouse that expresses human immunoglobulin genes rather than its own mouse immunoglobulin genes. Such transgenic mice, e.g., "HuMAb™" mice, contain human immunoglobulin gene mini-loci that encode unrearranged human heavy (μ and γ) and κ light chain immunoglobulin sequences, together with targeted mutations that inactivate the endogenous μ and κ chain loci (see, e.g., Lonberg, N. et al. *Nature* 368(6474): 856-859, 1994, and U.S. Pat. No. 5,770,429, which are incorporated herein by reference in their entirety). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (see, e.g., Lonberg, N. et al., supra; reviewed in Lonberg, N. *Handbook of Experimental Pharmacology* 113:49-101, 1994; Lonberg, N. and Huszar, D., *Intern. Rev. Immunol.,* 13: 65-93, 1995, and Harding, F. and Lonberg, N., *Ann. N.Y. Acad. Sci.,* 764:536-546, 1995, which are incorporated herein by reference in their entirety). To generate fully human monoclonal antibodies to an antigen, HuMAb mice can be immunized with an immunogen, as described by Lonberg, N. et al., *Nature,* 368(6474): 856-859, 1994; Fishwild, D. et al., *Nature Biotechnology,* 14: 845-851, 1996 and WO 98/24884. For example, a purified preparation of pIgA can be used to immunize the HuMAb mice intraperitoneally (IP). To generate antibodies against pIgA, mice can be immunized with a fragment of pIgA, e.g., the J chain of pIgA. The mouse splenocytes can be isolated and fused with PEG to a mouse myeloma cell line based upon standard protocols. The resulting hybridomas are then screened for the production of antigen-specific antibodies.

In one embodiment, the transgenic mouse will exhibit immunoglobulin production with a significant repertoire, ideally substantially similar to that of a native mouse. The repertoire in the transgenic mouse will ideally approximate that shown in a non-transgenic mouse, usually at least about 10% as high, preferably 25% to 50% or more as high. Generally, at least about a thousand different immunoglobulins (ideally IgG), preferably $10^4$ to $10^6$ or more, will be produced, depending primarily on the number of different V, J, and D regions introduced into the mouse genome. Typically, the immunoglobulins will exhibit an affinity for preselected antigens of at least about $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, or greater, e.g., up to $10^{-15}$ M or more. HuMAb mice can produce B cells that undergo class-switching via intra-transgene switch recombination (cis-switching) and express immunoglobulins reactive with pIgA. The human sequence antibodies that bind to pIgA can result from isotype switching, such that human antibodies comprising a human sequence gamma chain (such as gamma 1, gamma 2, or gamma 3) and a human sequence light chain (such as κ) are produced.

Anti-multimeric IgA antibodies can also be raised in other mammals, including non-transgenic mice, humans, rabbits, and goats. Indeed, it is specifically contemplated that antibodies can also be derived from B cells of immunized or infected subjects as an alternative to using HuMAb mice.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

6. Antibody Variants

In certain embodiments, amino acid sequence variants of the anti-pIgA antibodies of the invention are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, for example, to improve antibody affinity. Such alterations may be made in CDR "hotspots," i.e., residues encoded by codons that undergo mutation at high frequency during the somatic maturation process, and/or residues that contact antigen, with the resulting variant VH or VL being tested for binding affinity. Affinity maturation by constructing and reselecting from secondary libraries is known in the art. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two, or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, And Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, alternations may be made to the Fc region of an antibody. These alterations can be made alone, or in addition to, alterations to one or more of the antibody variable domains (i.e., VH or VL regions) or regions thereof (e.g., one or more CDRs or FRs). The alterations to the Fc region may result in enhanced antibody effector functions (e.g., complement-dependent cytotoxicity (CDC)), for example, by increasing C1q avidity to opsonized cells. Exemplary mutations that enhance CDC include, for example, Fc mutations E345R, E430G, and S440Y. Accordingly, anti-pIgA antibodies of the invention may contain one or more CDC-enhancing Fc mutations, which promote IgG hexamer formation and the subsequent recruitment and activation of C1, the first component of complement (see, e.g., Diebolder et al. *Science.* 343: 1260-1263, 2014).

In certain embodiments, alterations of the amino acid sequences of the Fc region of the antibody may alter the half-life of the antibody in the host. Certain mutations that alter binding to the neonatal Fc receptor (FcRn) may extend half-life of antibodies in serum. For example, antibodies that have tyrosine in heavy chain position 252, threonine in position 254, and glutamic acid in position 256 of the heavy chain can have dramatically extended half-life in serum (see, e.g., U.S. Pat. No. 7,083,784).

7. Production and Modification of Antibodies

Anti-pIgA antibodies or portions thereof useful in the present invention can also be recombinant antibodies produced by host cells transformed with DNA encoding immunoglobulin light and heavy chains of a desired antibody. Recombinant antibodies may be produced by known genetic engineering techniques, as described, for example, in U.S. Pat. No. 4,816,567, which is herein incorporated by reference in its entirety. For example, recombinant antibodies can be produced by cloning a nucleotide sequence, e.g., a cDNA or genomic DNA, encoding the immunoglobulin light and heavy chains of the desired antibody. The nucleotide sequence encoding those polypeptides may be manipulated if desired (e.g., cloned to switch from one isotype to another, e.g., cloned to switch from an IgG3 class isotype to an IgG1 class isotype), and is then inserted into an expression vector so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is preferred because such cells are more likely than prokaryotic cells to assemble and secrete a properly folded and immunologically active antibody. However, any antibody produced that is inactive due to improper folding can be renatured according to well-known methods (Kim and Baldwin, *Ann. Rev. Biochem.* 51: 459-89, 1982, which is herein incorporated by reference in its entirety). It is possible that the host cells will produce portions of intact antibodies, such as light chain dimers or heavy chain dimers, which also are antibody homologs according to the present invention.

The antibodies described herein also can be produced in a host cell transfectoma using, for example, a combination of recombinant DNA techniques and gene transfection methods as is well known in the art (Morrison, S., *Science,* 229: 1202, 1985, which is herein incorporated by reference in its entirety). For example, in one embodiment, the gene(s) of interest, e.g., human antibody genes, can be ligated into an expression vector such as a eukaryotic expression plasmid such as used in a GS gene expression system disclosed in WO 87/04462, WO 89/01036, and EP 338 841, which are herein incorporated by reference in their entirety, or in other expression systems well known in the art. In another example, the antibody genes of interest can be selected (e.g., by methotrexate selection) in eukaryotic host cells, such as CHO cells. The purified plasmid with the cloned antibody genes can be introduced in eukaryotic host cells such as CRO-cells or NSO-cells or alternatively other eukaryotic cells like a plant derived cells, fungi, or yeast cells. The method used to introduce these genes can be any method described in the art, such as electroporation, lipofectine, lipofectamine, transfection (e.g., calcium chloride-mediated), or ballistic transfection, in which cells are bombarded with microparticles carrying the DNA of interest (Rodin, et al. *Immunol. Lett.* 74(3): 197-200, 2000, which is herein incorporated by reference in its entirety). After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells using standard techniques.

It will be understood that variations on the above procedures are useful in the present invention. For example, it may be desired to transform a host cell with DNA encoding either the light chain or the heavy chain (but not both) of an antibody. Recombinant DNA technology may also be used to remove some or all of the DNA encoding either or both of the light and heavy chains that is not necessary for binding, e.g., the constant region may be modified by, for example, deleting specific amino acids. The molecules expressed from such truncated DNA molecules are useful in the methods described herein. In addition, bifunctional antibodies can be produced in which one heavy and one light chain bind to the pIgA, and the other heavy and light chain are specific for an antigen other than the pIgA, or another epitope of the pIgA.

As described above, also within the scope of the invention are antibodies in which specific amino acids have been substituted, deleted, or added. In particular, preferred antibodies have amino acid substitutions in the framework region, such as to improve binding to the antigen. For example, a selected, small number of acceptor framework residues of the immunoglobulin chain can be replaced by the corresponding donor amino acids. Preferred locations of the substitutions include amino acid residues adjacent to the CDR, or which are capable of interacting with a CDR (see, e.g., U.S. Pat. No. 5,585,089, which is herein incorporated by reference in its entirety). Criteria for selecting amino acids from the donor are described in U.S. Pat. No. 5,585,089 (e.g., col. 12-16). The acceptor framework can be a mature human antibody framework sequence or a consensus sequence. As desired, the Fc region of antibodies of the invention can be altered to modulate effector function(s) such as, for example, complement binding and/or Fc receptor binding. Criteria and subsets of framework alterations and/or constant regions suitable for alteration (by, e.g., substitution, deletion, or insertion) are described in U.S. Pat. Nos. 6,548,640; 5,859,205; 6,632,927; 6,407,213; 6,054,297; 6,639,055; 6,737,056; and 6,673,580, which are herein incorporated by reference in their entirety.

An anti-pIgA antibody, or an antigen-binding portion thereof, can be derivatized or linked to another functional molecule (e.g., another peptide or protein). For example, an antibody can be functionally linked (by chemical coupling, genetic fusion, non-covalent association or otherwise) to one or more other molecular entities, such as another antibody, a detectable agent, a cytotoxic agent, a pharmaceutical agent, and/or a protein or peptide that can mediate association with another molecule (such as a streptavidin core region or a polyhistidine tag). One type of derivatized antibody (or fragment thereof) is produced by crosslinking two or more of such proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, IL.

Useful detectable agents with which an antibody or fragment thereof can be derivatized (or labeled) include fluorescent compounds, various enzymes, prosthetic groups, luminescent materials, bioluminescent materials, and radioactive materials. Exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, 13-galactosidase, acetylcholinesterase, glucose oxidase and the like. When a protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A protein can also be derivatized with a prosthetic group (e.g., streptavidin/biotin and avidin/biotin). For example, an antibody can be derivatized with biotin, and detected through indirect measurement of avidin or streptavidin binding.

Labeled proteins and antibodies can be used, for example, diagnostically and/or experimentally in a number of contexts, including (i) to isolate a predetermined antigen by standard techniques, such as affinity chromatography or immunoprecipitation; and (ii) to detect a predetermined antigen (e.g., pIgA, (e.g., a dIgA or sIgA antibody), or the J chain of a pIgA antibody (e.g., the J chain of a dIgA or sIgA antibody)) in a cellular lysate or a patient sample.

Any of the above protein derivatizing/labeling techniques can also be employed on the target (i.e., the pIgA (e.g., dIgA or sIgA) or fragment(s) thereof (e.g., the J chain of a pIgA antibody).

B. Screening, Selection, and Purification Methods

Anti-pIgA antibodies can be characterized for binding to pIgA (e.g., dIgA or sIgA) by a variety of known techniques. Antibodies are typically characterized by ELISA first. Briefly, micro titer plates can be coated with the target antigen in PBS, for example, pIgA (e.g., dIgA or sIgA), or a portion thereof (e.g., the J chain thereof), and then blocked with irrelevant proteins such as bovine serum albumin (BSA) diluted in PBS. Dilutions of plasma from mice immunized with the target antigen, for example, pIgA (e.g., dIgA or sIgA), or a portion thereof (e.g., the J chain thereof), are added to each well and incubated for 1-2 hours at 37° C. The plates are washed with PBS/TWEEN® 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with pIgA (e.g., dIgA or sIgA). Hybridomas that produce antibodies that bind, preferably with high affinity, to pIgA can then be subcloned and further characterized. One clone from each hybridoma, which retains the reactivity of the parent cells (by ELISA), can then be chosen for making a cell bank, and for antibody purification.

To purify the anti-pIgA antibodies, selected hybridomas can be grown in roller bottles, spinner-flasks, or other culture systems. Supernatants can be filtered and concentrated before affinity chromatography with protein A-Sepharose (Pharmacia, Piscataway, N.J.) to purify the protein. After buffer exchange to PBS, the concentration can be determined by spectrophotometric methods.

To determine if the selected monoclonal antibodies bind to unique epitopes, each antibody can be biotinylated using commercially available reagents (Pierce, Rockford, Ill.). Biotinylated MAb binding can be detected with a streptavidin labeled probe. Anti-pIgA antibodies can be further tested for reactivity with the pIgA by immunoprecipitation or immunoblot. Particular antibodies of the invention are characterized as binding to the J chain of an intact dIgA or sIgA antibody.

C. Methods of Detection and Purification of pIgA

In certain embodiments, the anti-pIgA antibody of the invention is useful for in vitro or in vivo detection of the presence of pIgA (e.g., dIgA or sIgA) in a sample. The term "detecting" as used herein encompasses quantitative or qualitative detection. In certain embodiments, the sample is a biological sample and comprises a cell or tissue.

In one embodiment, a method of detecting the presence of pIgA (e.g., dIgA or sIgA) in a sample is provided. In certain embodiments, the method comprises contacting the sample with an anti-pIgA antibody as described herein under conditions permissive for binding of the anti-pIgA antibody to pIgA, and detecting whether a complex is formed between the anti-pIgA antibody and the pIgA. Such a method may be an in vitro or in vivo method. In other embodiments, a method of purifying pIgA from a sample is provided, wherein the method includes contacting the sample with an anti-pIgA antibody as described herein under conditions permissive for binding of the anti-pIgA antibody to pIgA. Also provided is a method of quantitating pIgA in a sample including contacting the sample with an anti-pIgA antibody as described herein under conditions permissive for binding of the anti-pIgA antibody to pIgA. The sample can be an antibody preparation, plasma, or a mucosal secretion, and can, e.g., be isolated from a human. In further embodiments, a fragment of an anti-pIgA antibody (e.g., a Fab) or a full-length anti-pIgA antibody may be immobilized to a surface (e.g., a Sephraose bead, e.g., for use in an immunoaffinity column).

In certain embodiments, labeled anti-pIgA antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

D. Compositions and Kits

In another aspect of the invention, the invention provides a composition including an anti-pIgA antibody as described herein. Compositions and formulations of the anti-pIgA antibody can be prepared in the form of lyophilized formulations or aqueous solutions. For example, the composition of the anti-pIgA antibody includes buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose, or sorbitol; salt-forming counter-ions such as sodium; metal complexes (e.g., Zn-protein complexes); and/or non-ionic surfactants such as polyethylene glycol (PEG). Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In yet another aspect of the invention, the invention provides a kit comprising an antibody of the invention and a package insert with instructions for using the antibody for purifying pIgA from a sample. In another example, the invention provides a kit comprising an antibody of the invention and a package insert with instructions for using the antibody for quantitating pIgA content in a sample. The sample can be an antibody preparation, plasma, or a mucosal secretion, and can, e.g., be isolated from a human.

Other embodiments of the present invention are described in the following Examples. The present invention is further illustrated by the following examples which should not be construed as further limiting. The contents of Sequence Listing, figures and all references, patents and published patent applications cited throughout this application are expressly incorporated herein by reference.

III. Examples

The following are examples of the methods and compositions of the invention. It is understood that various other embodiments may be practiced, given the description provided herein.

Example 1

Generation of Anti-Polymeric IgA (pIgA) Antibodies

An immunogen was developed in which the human J chain coding region (SEQ ID NO: 33; UniProt No. P01591, without the natural signal sequence of MKNHLLFWGV-LAVFIKAVHVKA) was cloned into pMAL-5 vector resulting in a maltose binding protein (MBP) fusion protein using standard techniques.

The J chain-MBP product was purified by binding to amylose, quantitated by NANODROP™ and mixed with RIBI adjuvant using standard methods and used to immunize mice. Mice were immunized with 50 µg/ml J chain-MBP fusion protein intraperitoneally (i.p.), with boosts of 25 µg/ml every week for three weeks. Mice were boosted with J chain-MBP intravenously (i.v.) and i.p. three days and two days prior to fusion. Four separate fusions were performed with 4 different mice (CA1L, CA1RL, CA1LL, and CA1NP) using a 3:1 ratio of splenocytes to fusion partner (P3X) with 40 plates per fusion. Supernatants from resulting hybridomas were screened for reactivity against dIgA. The results of screening are as follows:

CA1L (~30% growth); 35+ from 96 wells, all transferred to 48 wells. 14+ out of 48 wells, transferred to 24 wells. 4 repeated out of 24 wells yielding 4 positive producing antibodies.

CA1RL (~15% growth); 7+ from 96 wells and moved to 48 wells, 1 repeated from 48 well and transferred to 24 well where it lost production. 0 antibodies.

CA1LL (~80% growth); 24+ from 96 wells and moved to 48 wells. 5+ from 48 wells and moved to 24 wells, lost one yielding 4 positive producing antibodies.

CA1NP (30% growth); 7+ from 96 well and moved to 48 wells. Only 2 repeated from 24 well stage, yielding 2 positive producing antibodies.

Figure 4:
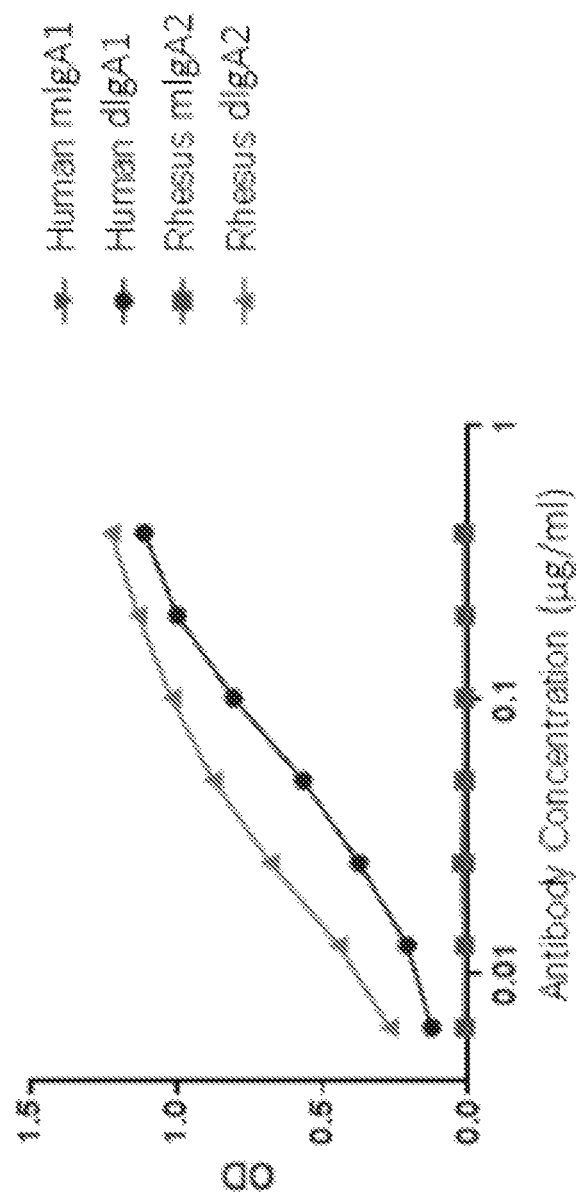
FIG. 4 is a graph showing specific reactivity of the CA1L 33e1 A1a3 antibody with human and rhesus dIgA, but not human or rhesus mIgA.

Of these, two hybridomas continued production on expansion into tissue culture flasks, CA1L 33e1 and CA1LL 23h8. Both hybrids were tested further for reactivity with dIgA1 and dIgA2 (FIG. 1), as well as rhesus dIgA and mIgA (FIG. 4), to ensure specificity.

Figure 2:
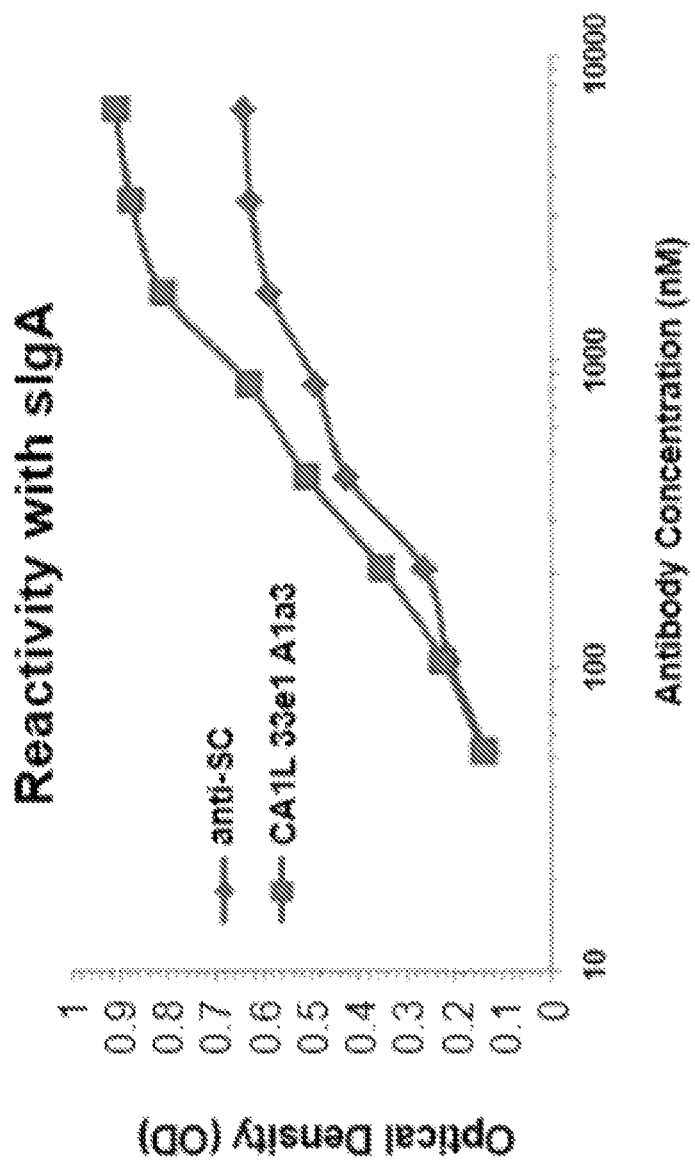
FIG. 2 is a graph showing reactivity of the CA1L 33e1 A1a3 antibody with secretory IgA (sIgA).

Both antibodies failed to react with monomeric IgA. CA1L 33e1 was picked as the lead antibody based on its higher reactivity with human dIgA (both human dIgA1 and dIgA2, as shown in FIG. 1). The hybridoma was cloned by limiting dilution to isolate a high-producing homogenous clone. The clone selected was CA1L 33e1 A1a3. As shown in FIG. 2, the antibody also reacts with sIgA.

Figure 3:
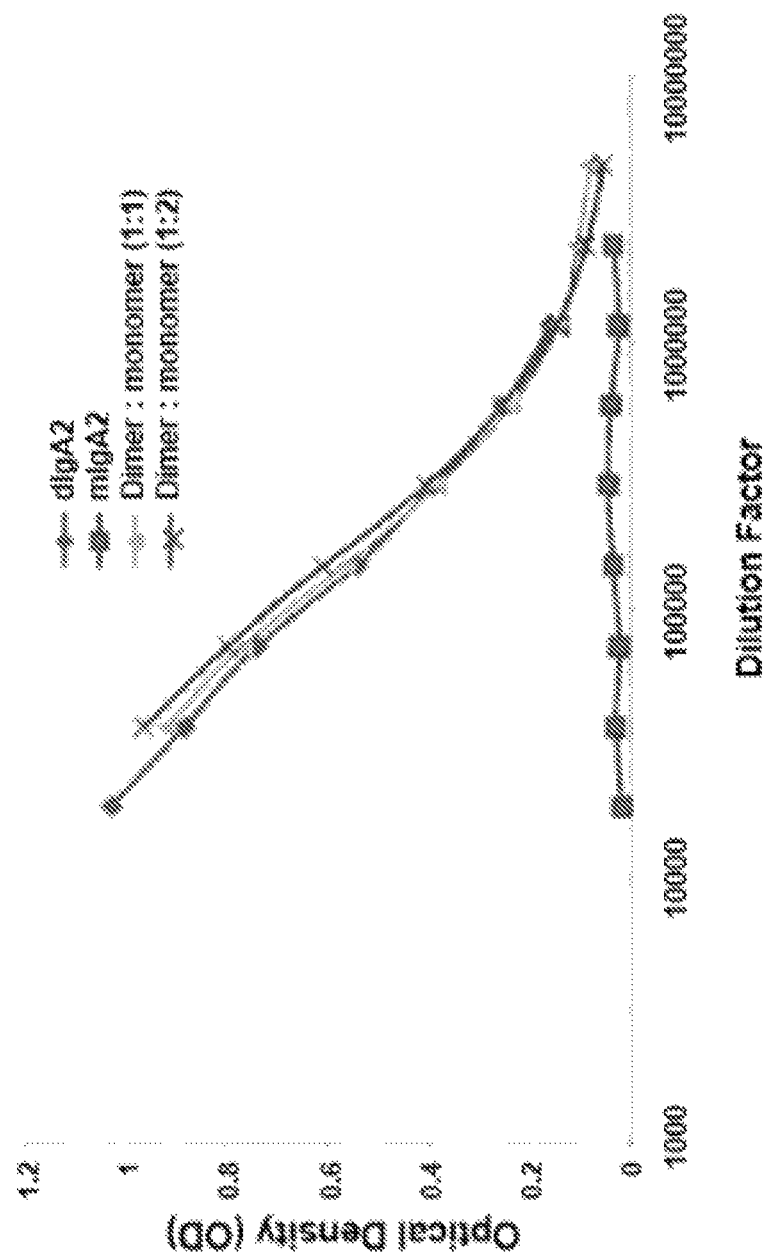
FIG. 3 is a graph showing reactivity of the CA1L 33e1 A1a3 antibody with monomeric IgA (mIgA) alone, dIgA alone, a 1:1 mixture of mIgA and dIgA, and a 1:2 mixture of mIgA and dIgA.

Based on the reactivity of the CA1L 33e1 A1a3 antibody with dIgA and not mIgA, an enzyme-linked immunosorbent assay (ELISA) was developed to quantitate dIgA in a mixed solution as would be expected for antibody-expressing cell supernatant, serum, plasma, or mucosal secretions. ELISA plates were coated at 1 µg/mL with CA1L 33e1 A1a3 antibody. Dimer alone, a mix of monomer and dimer at ratios of 1:1 and 1:2, and monomer alone were serially diluted on the plate. Bound dimeric antibody was detected using a goat anti-human IgA horseradish peroxidase (HRP) antibody at 1:30,000 dilution. 3,3',5,5'-tetramethylbenzidine (TMB) substrate was used to develop the plate and optical density at 490 nm was measured using a plate reader. Data are shown in FIG. 3.

Figure 5:
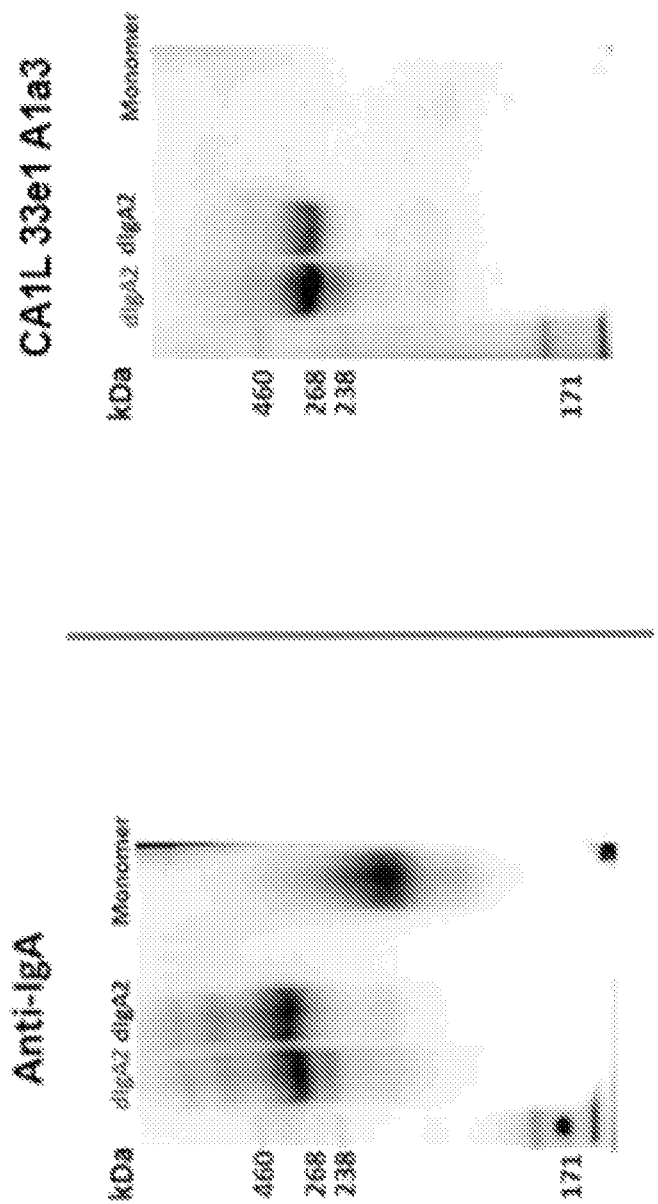
FIG. 5 is a set of Western blots showing specific reactivity of CA1L 33e1 A1a3 with only dIgA but not mIgA (right panel), as compared to a control goat anti-human IgA antibody that reacts with both mIgA and dIgA (left panel).

RNA from the clone cells was used to generate cDNA for sequencing of the antibody genes. Based on the sequence, the heavy chain variable domain utilizes the IGHV5-9-1*02, IGHJ2*01, IGHD1-1*01 gene families; the light chain variable domain utilizes gene families IGKV12-41*01 and IGKJ2*03. The antibody described herein reacts by Western blot with dIgA, as well as with the J chain of intact dIgA by ELISA. Furthermore, the antibody reacts with human and rhesus dIgA, including both A1 and A2 subclasses for human IgA, but not human mIgA, as demonstrated by Western blot (FIG. 5).

Example 2

Effect of Antibody Isotype, Multimerization, and Variable Region Evaluated Using an In Vitro Gastrointestinal Stability Assay The following provides an example of the use of the anti-pIgA antibodies described herein for selecting pIgA antibodies.

The development of monoclonal antibodies (mAbs) for prophylactic or therapeutic use is expanding rapidly. To date, all mAbs are administered via injection, which can result in some challenges, including the elicitation of undesirable off-target effects and the development of immune responses against the mAbs themselves. MAb delivery via oral administration represents an attractive alternative, particularly for gastrointestinal disorders and against enteric pathogens in terms of ease of use, enabling specific targeting of the mAb to affected sites at high concentrations, and minimizing off-target effects. A significant obstacle for oral delivery is the gastrointestinal environment itself, where low pH and pepsin in the stomach and multiple proteases in the intestine can rapidly degrade proteins. Antibodies that occur naturally on mucosal surfaces, particularly secretory IgAs, have evolved protective mechanisms to resist such degradation, and may offer a platform for oral delivery of antibodies with enhanced gastrointestinal stability.

To evaluate the influence of antibody isotype and multimerization state on mAb stability in the upper intestine, an in vitro assay was developed using simulated intestinal fluid (SIF) containing porcine pancreatin. MAbs were produced as IgG, monomeric (m)IgA1 and mIgA2, dIgA1 and dIgA2, and sIgA1 and sIgA2. Four different mAbs were evaluated for stability over two hours. It was observed that IgG was the most susceptible to degradation, while sIgA tended to be the most stable over time, and mIgA and dIgA were intermediate in stability. The anti-pIgA antibody CA1L 33e1, described in Example 1, was used to detect the dIgA and sIgA antibodies used in this experiment. Interestingly, while all mAbs contained identical Fc regions, differences in stability between the individual mAbs were observed, suggesting that the variable region may also influence stability. Overall, these results provide insights into optimization strategies for intestinal stability, and in combination with formulation for gastric stability can lead to the development of effective strategies for the oral delivery of mAbs.

Example 3

The Effect of Formulation on sIgA Stability

The following provides an example of the use of the anti-pIgA antibodies described herein for selecting and quantitating pIgA antibodies. Quantitating pIgA antibodies was previously not possible.

Enterotoxigenic *Escherichia coli* (ETEC) is a leading cause of diarrhea-associated illness in developing countries. There is currently no vaccine licensed to prevent ETEC and the development of an efficacious prophylaxis would provide an intervention with significant impact. We previously identified a panel of human monoclonal antibodies in both IgG1 and secretory IgA (sIgA) forms, with efficacy to block colonization and prevent ETEC diarrhea. These antibodies are currently under development as potential immunoprophylaxis against ETEC. Of particular interest is the development of the anti-ETEC sIgA as an oral prophylaxis for mucosal immunity.

Here, studies were performed to test the feasibility of formulating sIgA for oral delivery. The anti-pIgA antibody CA1L 33e1, described in Example 1, was used to detect and quantitate the sIgA antibodies used in this experiment. Lyophilization was used as a method of preserving antibody functionality for storage. Various formulation conditions and lyophilization parameters were tested and compared for their impact on sIgA1 and sIgA2 binding and function. Our study demonstrates the possibility of delivery sIgA as an oral medicine when properly formulated.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that specifically binds polymeric immunoglobulin A (pIgA), wherein the antibody comprises the following complementarity determining regions (CDRs):
   (a) a CDR-H1 comprising the amino acid sequence of GFTFSNYG (SEQ ID NO: 1);
   (b) a CDR-H2 comprising the amino acid sequence of INRGGDRI (SEQ ID NO: 2);
   (c) a CDR-H3 comprising the amino acid sequence of RGLYYYGSDYYFDY (SEQ ID NO: 3);
   (d) a CDR-L1 comprising the amino acid sequence of GNIHNY (SEQ ID NO: 4);
   (e) a CDR-L2 comprising the amino acid sequence of NAK (SEQ ID NO: 5); and
   (f) a CDR-L3 comprising the amino acid sequence of HHYYSTPYT (SEQ ID NO: 6).

2. The antibody of claim 1, wherein the antibody further comprises the following heavy chain framework regions (FRs):
   (a) an FR-H1 comprising the amino acid sequence of DVKLVESGEGLVKPGGSLKLSCVAS (SEQ ID NO: 7);
   (b) an FR-H2 comprising the amino acid sequence of MSWVRQTPEKRLEWVAF (SEQ ID NO: 8);
   (c) an FR-H3 comprising the amino acid sequence of YYADTVKGRFTISRDNARNTLYLQMSSLKSED-TAIYYC (SEQ ID NO: 9); and
   (d) an FR-H4 comprising the amino acid sequence of WGQGTTLTVSS (SEQ ID NO: 10); and/or comprises the following light chain FRs:
   (a) an FR-L1 comprising the amino acid sequence of DIQMTQSPASLSTSVGETVTITCRAS (SEQ ID NO: 11);
   (b) an FR-L2 comprising the amino acid sequence of LAWSQQKQGNSPOLLVY (SEQ ID NO: 12);
   (c) an FR-L3 comprising the amino acid sequence of TLAEGVPSRFSGSGSGTQYSLKINSLOPE-DFGSYYC (SEQ ID NO: 13); and
   (d) an FR-L4 comprising the amino acid sequence of FGSGTKLEIK (SEQ ID NO: 14).

3. The antibody of claim 1, wherein the antibody comprises a heavy chain variable (VH) domain comprising an amino acid sequence having at least 95% sequence identity to the amino acid sequence of SEQ ID NO: 15 and a light chain variable (VL) domain comprising an amino acid sequence having at least 95% sequence identity to the amino acid sequence of SEQ ID NO: 16.

4. The antibody of claim 1, wherein the pIgA is a dimeric IgA (dIgA) or a secretory IgA (sIgA).

5. The antibody of claim 1, wherein:
   (a) the antibody specifically binds to a J chain polypeptide of pIgA:
   (b) the antibody binds to intact pIgA; and/or
   (c) the pIgA is a human or a rhesus pIgA.

6. The antibody of claim 1, wherein the antibody is a monoclonal, human, humanized, or chimeric antibody, and/or is an IgG antibody.

7. The antibody of claim 1, wherein the antibody is a full-length antibody or an antibody fragment that specifically binds pIgA.

8. The antibody of claim 1, wherein:
   (a) the antibody is cross-reactive with human pIgA and rhesus pIgA; and/or
   (b) the antibody does not bind monomeric IgA (mIgA).

9. An isolated antibody that specifically binds pIgA, wherein the antibody comprises a VH domain comprising the amino acid sequence of SEQ ID NO: 15 and a VL domain comprising the amino acid sequence of SEQ ID NO: 16.

10. A composition comprising the antibody of claim 1.

11. An isolated nucleic acid encoding the antibody of claim 1.

12. A vector comprising the nucleic acid of claim 11.

13. A host cell comprising the vector of claim 12.

14. A method of producing an antibody that specifically binds pIgA, the method comprising culturing the host cell of claim 13 in a culture medium.

15. A method of purifying pIgA from a sample or quantitating pIqA in a sample, the method comprising contacting the sample with the antibody of claim 1.

16. The method of claim 15, wherein the sample is an antibody preparation, a plasma sample, or a mucosal secretion sample, and/or wherein the sample is isolated from a human.

17. The method of claim 15, wherein the pIgA is dIgA or sIgA.

18. A kit comprising the antibody of claim 1 and a package insert comprising:
   (a) instructions for using the antibody for purifying pIgA from a sample; or
   (b) instructions for using the antibody for quantitating pIgA in a sample.

19. The kit of claim 18, wherein the sample is an antibody preparation, a plasma sample, or a mucosal secretion sample, and/or the sample is isolated from a human.

20. The kit of claim 18, wherein the pIgA is dIgA or sIgA.

* * * * *

UNITED STATES PATENT AND TRADEMARK OFFICE
CERTIFICATE OF CORRECTION

| | | |
|---|---|---|
| PATENT NO. | : 12,168,699 B2 | Page 1 of 1 |
| APPLICATION NO. | : 17/598385 | |
| DATED | : December 17, 2024 | |
| INVENTOR(S) | : Cavacini et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 740 days.

Signed and Sealed this
Seventh Day of October, 2025

John A. Squires
*Director of the United States Patent and Trademark Office*